(12) United States Patent
Zabudkin et al.

(10) Patent No.: US 9,765,083 B2
(45) Date of Patent: Sep. 19, 2017

(54) METHOD FOR THE SYNTHESIS OF IRINOTECAN

(71) Applicant: Synbias Pharma AG, Schaffhausen (CH)

(72) Inventors: Alexander Zabudkin, Donetsk (UA); Viktor Matvienko, Donetsk (UA)

(73) Assignee: Synbias Pharma AG, Schaffhausen (CH)

( * ) Notice: Subject to any disclaimer, the term of this patent is extended or adjusted under 35 U.S.C. 154(b) by 0 days.

(21) Appl. No.: 15/023,827

(22) PCT Filed: Nov. 24, 2014

(86) PCT No.: PCT/EP2014/075369
§ 371 (c)(1),
(2) Date: Mar. 22, 2016

(87) PCT Pub. No.: WO2015/082240
PCT Pub. Date: Jun. 11, 2015

(65) Prior Publication Data
US 2016/0264590 A1 Sep. 15, 2016

(30) Foreign Application Priority Data
Dec. 3, 2013 (EP) .................................. 13195464

(51) Int. Cl.
| | | |
|---|---|---|
| *C07D 471/00* | (2006.01) | |
| *C07D 491/00* | (2006.01) | |
| *C07D 498/00* | (2006.01) | |
| *C07D 513/00* | (2006.01) | |
| *C07D 515/00* | (2006.01) | |
| *A61K 31/44* | (2006.01) | |
| *C07D 491/22* | (2006.01) | |

(52) U.S. Cl.
CPC .................................. *C07D 491/22* (2013.01)

(58) Field of Classification Search
None
See application file for complete search history.

(56) References Cited

U.S. PATENT DOCUMENTS

2005/0272757 A1  12/2005  Naidu

FOREIGN PATENT DOCUMENTS

| CN | 102718772 | 10/2012 |
| EP | 0137145 | 4/1985 |
| WO | WO-2005/019223 | 3/2005 |
| WO | WO-2006/016203 A1 | 2/2006 |
| WO | WO-2008/035377 | 3/2008 |
| WO | WO-2015/082240 | 6/2015 |

OTHER PUBLICATIONS

Rao, Avr. et al. Scalable Synthetic Route to 2-Amino-5-hydroxypropiophenone: Efficient Formal Synthesis of Irinotecan. Synthetic Communications. 2013, vol. 43, p. 1662.*

"International Application No. PCT/EP2014/075369, International Search Report and Written Opinion mailed Jan. 7, 2015", (Jan. 7, 2015), 9 pgs.

"European Application No. 14802435.9, Communication Under Rule 71(3) EPC dated Jun. 17, 2016", (Jun. 17, 2016), 7 pgs.

"European Application No. 14802435.9, Decision to grant a European patent dated Aug. 19, 2016", (Aug. 19, 2016), 2 pgs.

* cited by examiner

*Primary Examiner* — Noble Jarrell
*Assistant Examiner* — Ben S Michelson
(74) *Attorney, Agent, or Firm* — Edell, Shapiro & Finnan, LLC.

(57) ABSTRACT

The present invention relates to a method for the synthesis of 7-ethyl-10-[4-(1-piperidino)-1-piperidino]carbonyloxycamptothecin (i.e. irinotecan), comprising: (a) preparing 10-[4-(1-piperidino)-1-piperidino]carbonyloxycamptotecin; and (b) selectively ethylating the compound of step (a) at the 7-position, thus resulting in the preparation of 7-ethyl-10-[4-(1-piperidino)-1-piperidino]carbonyloxycamptothecin. The present invention is further directed to the use of 10-[4-(1-piperidino)-1-piperidino]carbonyloxycamptothecin (i.e. 7-des-ethyl-irinotecan) as intermediate in a method for the synthesis of irinotecan as described.

7 Claims, 3 Drawing Sheets

METHOD FOR THE SYNTHESIS OF IRINOTECAN

PRIORITY CLAIM TO RELATED APPLICATIONS

This application is a U.S. national stage application filed under 35 U.S.C. §371 from International Application Ser. No. PCT/EP2014/075369, which was filed 24 Nov. 2014, and published as WO2015/082240 on 11 Jun. 2015, and which claims priority to European Application No. 13195464.6, filed 3 Dec. 2013, which applications and publication are incorporated by reference as if reproduced herein and made a part hereof in their entirety, and the benefit of priority of each of which is claimed herein.

FIELD OF THE INVENTION

The present invention is directed to a method for the synthesis of 7-ethyl-10-[4-(1-piperidino)-1-piperidino]carbonylcamptothcin, also referred to as irinotecan.

BACKGROUND OF THE INVENTION

Camptothecin is a cytotoxic quinoline alkaloid which inhibits the enzyme topoisomerase I. Camptothecin is naturally isolated from the bark and stem of *Camptotheca acuminate* (also referred to as "Happy Tree") and used as a cancer treatment in traditional Chinese medicine. Camptothecin shows remarkable anticancer activity in preliminary clinical trials but also low solubility and considerable adverse side effects. Because of these disadvantages various semi-synthetic derivatives have been developed in order to increase the clinical benefits. Two of these semisynthetic derivatives have meanwhile been approved for use in chemotherapy, namely topotecan and irinotecan (reviewed, e.g., in Ulukan, H. and Swaan P. W. (2002). *Drugs* 62, 2039-2057).

7-Ethyl-10-[4-(1-piperidino)-1-piperidino] carbonyloxycamptothecin, that is, irinotecan, has a chemical structure according to Formula 1.

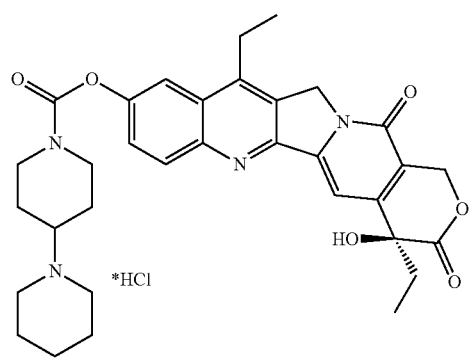

Formula 1

Irinotecan

Currently available methods for the synthesis of irinotecan comprise the preparation of 7-ethyl-10-hydroxycamptothecin as intermediate product, to which 4-(1-piperidino)-1-piperidine is attached at the 10-position.

7-ethyl-10-hydroxycamptothecin is also commonly referred to as compound "SN 38" having a chemical structure according to Formula 2. SN38 is the therapeutically active "component" of irinotecan that exhibits cytostatic activity. On the other hand, however, SN38 is characterized by a low solubility in water and most other solvents that significantly interferes with the applicability of known synthesis schemes with respect to overall yield and purity of the final reaction product.

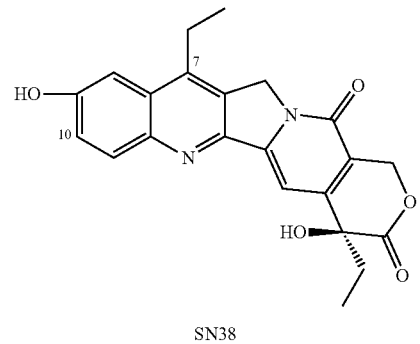

Formula 2

SN38

In order to prepare SN38, there are several ways of attaching the respective 7-ethyl and 10-hydroxyl groups to camptothecin which is used as a starting material.

A first synthesis route that is schematically illustrated in FIG. 1 comprises the introduction of a hydroxyl group at the 10-position of campothecin by means of a catalytic hydrogenation, followed by oxidation of the intermediate compound 1,2,6,7-tetrahydrocamptothecin by means of iodobenzene derivatives, thus resulting in the production of 10-hydroxycamptothecin. Subsequently, the 7-position of camptothecin is ethylated with propionic aldehyde in the presence of hydrogen peroxide or other peroxides and ferrous sulfate (i.e. iron(II) sulfate), that is, by means of classical Fenton's chemistry (Fenton, H. J. H. (1894) *J. Chem. Soc. Trans.* 65, 899-911).

A second synthesis route that is schematically illustrated in FIG. 2 comprises the ethylation of the 7-position of camptothecin with propionic aldehyde in the presence of hydrogen peroxide or other peroxides and ferrous sulfate (Fenton, H. J. H. (1894) supra), followed by introduction of a hydroxyl radical at the 10-position by a catalytic hydrogenation of 7-ethylcamptothecin, thus resulting in 7-ethyl-1,2,6,7-tetrahydrocamptothecin, and subsequent oxidation by means of, e.g., iodosobenzene, sodium periodate, or potassium peroxodisulfate. The overall yield of the desired reaction product SN38 is about 60% and purity is about 90%, respectively. This reaction pathway is further described inter alia in European patent 0 137 145 B1; U.S. Pat. No. 7,151,179 B2; U.S. Pat. No. 7,544,801 B2; and CN patent application 102718772 A.

Alternatively, the hydroxyl group at the 10-position of camptothecin can also be introduced photochemically. This scheme involves the oxidation of 7-ethyl-camptothecin which was prepared by employing the above-referenced Fenton's reaction in order to obtain 1-N-oxide-7-ethyl-camptothecin, followed by irradiation with ultraviolet light. This reaction pathway is further described inter alia in U.S. Pat. Nos. 4,473,692; and 4,545,880.

Yet another synthesis route is described in international patent publication WO 2005/019223. This pathway involves a condensation reaction of 7-ethyl-10-hydroxycamptothecin with 1-chlorocarbonyl-4-piperidinopiperidine hydrochloride in acetonitrile in the presence of 4-dimethylaminopyridine.

However, in all of the above methods, the yields are only at about 60-65% (as compared to the amount of starting material). Furthermore, the synthesis is significantly hampered by the low solubility of the reacting compounds. In order to overcome the latter problem, it was proposed to add acetic acid or trifluoroacetic acid as a co-solvent (Wu, D. (1998) *Cascade Radical Cyclization: Application in the Development of New Anticancer Drug of Camptotecin Family and Development of new Synthetic Method*. Master Thesis, University of Hawaii). This modification improved the reaction conditions but did not result in a significant increase of the overall yield.

For the subsequent synthesis of irinotecan, SN 38 is modified at the 10-position (i.e. the hydroxyl group) with a [4-(1-piperidino)-1-piperidino]carbonyl substituent according to Formula 3 by means of urea chloride or chloroformate in the presence of a strong organic base, such as triethylamine, 4-dimethylaminopyridine, or ethyldiisopropylamine).

Formula 3

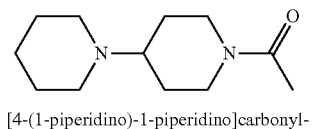

[4-(1-piperidino)-1-piperidino]carbonyl-

Nevertheless, the overall yield of these reaction schemes is still comparably low. Furthermore, reaction intermediates are common side products, thus reducing the purity of the desired reaction product irinotecan.

Thus, there is a need for improved methods for the synthesis of irinotecan that overcome the above-referenced limitations. In particular, there is a requirement for a synthesis pathway that allows for an efficient production of irinotecan in high purity.

Accordingly, it is an object of the present invention to provide such a method.

SUMMARY OF THE INVENTION

The present invention relates to a method for the synthesis of 7-ethyl-10-[4-(1-piperidino)-1-piperidino]carbonyloxy-camptothecin having the structure according to Formula 1, the method comprising:

Formula 1

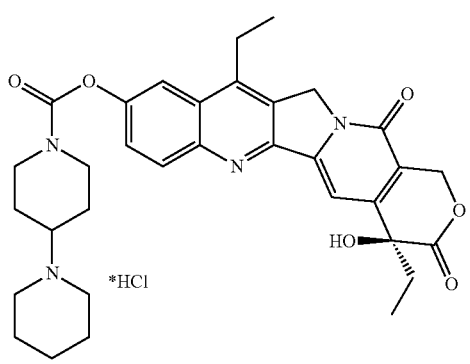

Irinotecan (a) preparing 10-[4-(1-piperidino)-1-piperidino]carbonyloxycamptothecin; and (b) selectively ethylating the compound of step (a) at the 7-position, thus resulting in the preparation of 7-ethyl-10-[4-(1-piperidino)-1-piperidino]carbonyloxy-camptothecin.

In a specific embodiment, 10-hydroxycamptothecin is used as starting material in step (a).

Preferably, when using 10-hydroxycamptothecin as starting material, step (a) is performed in acetonitrile in the presence of anhydrous carbonates of alkali metals or of a strong organic base. Particularly preferably, the anhydrous carbonates of alkali metals are selected from the group consisting of $Na_2CO_3$, $K_2CO_3$, $Rb_2CO_3$, and $Cs_2CO_3$; and the strong organic base is triethylamine.

In another preferred embodiment, step (a) is performed at a temperature in the range between 20° C. and 80° C., particularly preferably at 60° C.

In a particular preferred embodiment, step (b) is performed in the presence of ferrous sulfate, hydrogen peroxide, and propionic aldehyde.

In a particular preferred embodiment, step (b) is preceded by an esterification reaction at the C9-position.

The present invention is further directed to the use of 10-[4-(1-piperidino)-1-piperidino] carbonyloxycamptothecin as intermediate in a method for the synthesis of 7-ethyl-10-[4-(1-piperidino)-1-piperidino]carbonyloxycamptothecin as described herein.

DETAILED DESCRIPTION OF THE INVENTION

Figure 1:
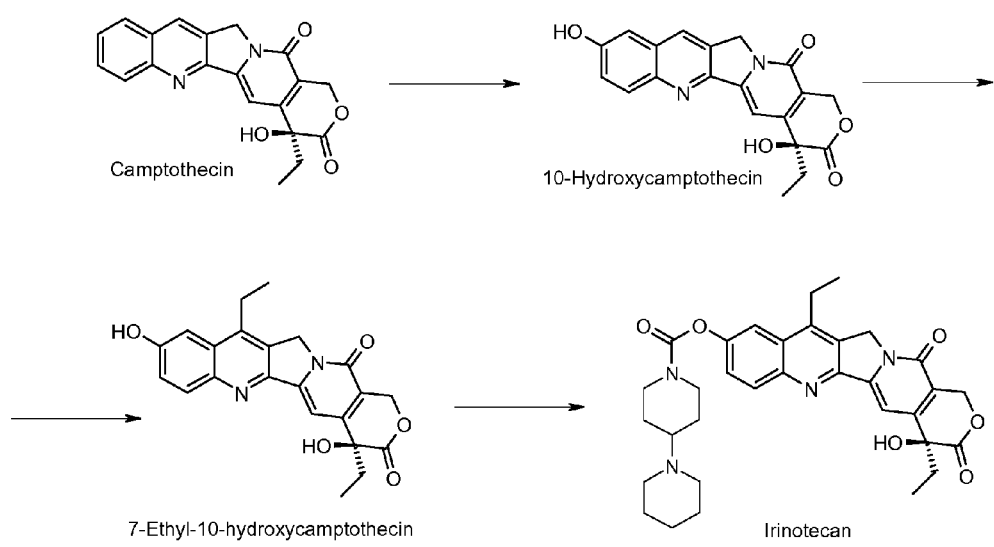
FIG. 1: Schematic representation of an established synthesis route for the preparation of 7-ethyl-10-[4-(1-piperidino)-1-piperidino]carbonyloxy-camptothecin that uses camptothecin as starting material and 10-hydroxycamptothecin as intermediate.

The present invention is related to the unexpected finding that 7-ethyl-10-[4-(1-piperidino)-1-piperidino]carbonylcamptothcin (i.e., irinotecan) can be produced in high overall yield of more than 90% and virtually without contaminating by-products. The synthesis pathway is characterized by the use of 10-hydroxycamptothecin as starting material and 10-[4-(1-piperidino)-1-piperidino]carbonyloxycamptotecin (i.e., 7-des-ethyl-irinotecan) as intermediate product for performing selective ethylation at the 7-position, thus interfering with the respective production of 11-ethyl-irinotecan and 7-ethyl-10-hydroxycamptothecin as adverse by-products.

The present invention will be described in the following with respect to particular embodiments and with reference to certain drawings but the invention is to be understood as not limited thereto but only by the appended claims. The drawings described are only schematic and are to be considered non-limiting.

Where the term "comprising" is used in the present description and claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun e.g. "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art.

In one aspect, the present invention relates to a method for the synthesis of 7-ethyl-10-[4-(1-piperidino)-1-piperidino] carbonyloxy-camptothecin having the structure according to Formula 1, the method comprising:

Formula 1

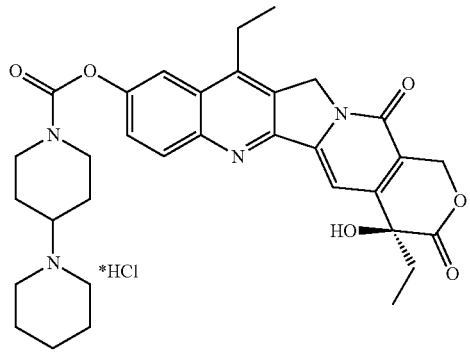

Irinotecan (a) preparing 10-[4-(1-piperidino)-1-piperidino]carbonyloxycamptothecin; and
(b) selectively ethylating the compound of step (a) at the 7-position, thus resulting in the preparation of 7-ethyl-10-[4-(1-piperidino)-1-piperidino]carbonyloxy-camptothecin.

Figure 3:
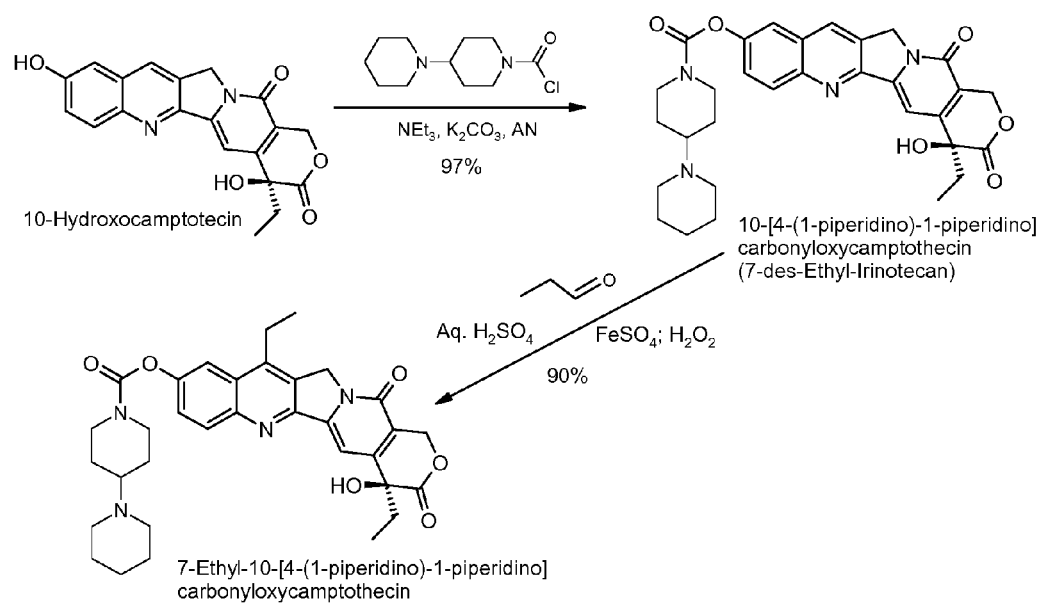
FIG. 3: Schematic representation of the synthesis route according to the presently claimed subject matter that uses 10-hydroxycamptothecin as starting material and 10-[4-(1-piperidino)-1-piperidino]carbonyloxycamptothecin as intermediate.

The overall reaction scheme of the method of the present invention is schematically illustrated in FIG. 3.

In a first step, the method of the present invention comprises the preparation of 10-[4-(1-piperidino)-1-piperidino]carbonyloxycamptothecin, that is, 7-des-ethyl-irinotecan.

In a specific embodiment, 10-hydroxycamptothecin is used as starting material for the preparation of 7-des-ethyl-irinotecan. 10-hydroxycamptothecin is an intermediate or byproduct in several other synthesis schemes, for example in the pathway illustrated in FIG. 1, and thus readily available. However, the use of other starting materials is possible as well, for example, the employment of camptothecin.

Subsequently, a [4-(1-piperidino)-1-piperidino]carbonyl substituent is attached to the hydroxyl group at the 10-position of 10-hydroxycamptothecin in order to obtain 7-des-ethyl-irinotecan.

In a preferred embodiment, this reaction step (i.e., when using 10-hydroxycamptothecin as starting material) is performed in acetonitrile in the presence of anhydrous carbonates of alkali metals or of a strong organic base. Any anhydrous carbonates of alkali metals or any strong organic base such as triethylamine, 4-dimethyl-aminopyridine, or ethyldiisopropylamine may be employed. Particularly preferably, the anhydrous carbonates of alkali metals are selected from the group consisting of $Na_2CO_3$, $K_2CO_3$, $Rb_2CO_3$, and $Cs_2CO_3$; and the strong organic base is triethylamine.

In another preferred embodiment, the attachment of the [4-(1-piperidino)-1-piperidino]carbonyl substituent is performed at a temperature in the range between 20° C. and 80° C., particularly preferably at a reaction temperature of 60° C.

The attachment of attachment of the [4-(1-piperidino)-1-piperidino]carbonyl substituent is a characterizing step of the method of the present invention with respect to an improvement of the selectivity for ethylation only occurring at the 7-position.

The presence of the bulky carboxy-piperidino-piperidine group in 7-des-ethyl-irinotecan interferes with or even completely blocks an unwanted ethylation at the 11-position (commonly also referred to as "known effect of ortho-position"), resulting in the undesired byproduct 11-ethyl-irinotecan which is produced in significant amounts in the synthesis pathways for irinotecan that are established in the art, which, in turn, requires the implementation of additional reaction steps in order to remove the byproduct.

It has also been found that 7-des-ethyl-irinotecan has a significantly better solubility as compared to camptothecin and 10-hydroxycamptothecin, respectively, which results in a reduction in the reaction volume required for performing the ethylation step. Finally, the carboxy-piperidino-piperidine group neutralizes the functionality of the 10-hydroxyl group as a trap for radicals which, in turn, would interfere with the subsequent ethylation at the 7-position.

In a second step, the method of the present invention comprises the selective ethylation of 1-des-ethyl-irinotecan at the 7-position, thus resulting in the preparation of 7-ethyl-10-[4-(1-piperidino)-1-piperidino]carbonyloxy-camptothecin, that is, irinotecan.

In a particular preferred embodiment, the ethylation reaction is performed in the presence of ferrous sulfate, hydrogen peroxide, and propionic aldehyde, that is, through classical Fenton's chemistry (Fenton, H. J. H. (1894) *J. Chem. Soc. Trans.* 65, 899-911) being well established in the art.

In a further particular preferred embodiment, the ethylation reaction is preceded by an esterification reaction at the C9-position in order to sterically interfere with an ethylation at the 11-position.

The method of the present invention results in an increase in overall yield of irinotecan of up to 90-92% (as compared to the starting material) as well as a significantly improved selectivity of the ethylation reaction, thus resulting in the virtual absence of the unwanted byproduct 11-ethyl irinotecan which is very difficult to separate in order to increase the purity of the irinotecan preparation.

In another aspect, the present invention is directed to the use of 10-[4-(1-piperidino)-1-piperidino] carbonyloxycamptothecin as intermediate in a method for the synthesis of 7-ethyl-10-[4-(1-piperidino)-1-piperidino]carbonyloxycamptothecin as described herein.

The invention is further described by the figures and the following examples, which are solely for the purpose of illustrating specific embodiments of this invention, and are not to be construed as limiting the claimed subject matter in any way.

EXAMPLES

Example 1

20 g of 10-hydroxycamptothecin are dissolved in 100 ml of acetonitrile, before adding 30 g of anhydrous $K_2CO_3$. Subsequently, a solution of 17.6 g of 1-chlorocarbonyl-4-piperidinopiperidine hydrochloride is added to 300 ml of acetonitrile under stirring. Stirring is continued for about 6 hours at 60° C.

Acetonitrile is evaporated, and the dry residue is dissolved in 200 ml dichloromethane. The organic layer is rinsed with 4×100 ml distilled water in order to remove non-organic impurities, and the solvent is evaporated. 400 ml of 40% $H_2SO_4$ are added to the dry residue at 20° C. After dissolution, 10.5 g of $FeSO_4 \times 7\ H_2O$ is added, cooled to −10° C. and mixed with 10 ml of propionic aldehyde.

The resulting solution of $H_2O_2$ and propionic aldehyde is cooled to 0° C. (75 ml of distilled water are cooled to 0° C. and 3.3 ml of 32% $H_2O_2$ and 5 ml of propionic aldehyde are added) and incubated in a smooth flowing manner for 150 min. The reaction product (i.e. irinotecan) is diluted with water to a volume of 3 l and transferred to chromatographic purification (Diaion sorbent resin).

Example 2

20 g of 10-hydroxycamptothecin are dissolved in 300 ml of acetonitrile. 20 ml of triethylamine are added along with 17.6 g of 1-chlorocarbonyl-4-piperidinopiperidine hydrochloride. Stirring is continued for about 2 hours at 60° C.

The reaction mass is evaporated to dryness. 300 ml of $H_2O$ are added and again evaporated. An aqueous solution of sulfuric acid (400 ml of 40% $H_2SO_4$) is added into the dry residue.

Then, 10.5 g of $FeSO_4 * 7H_2O$ are added at 20° C., cooled to −10° C. before propionic aldehyde is added (10 ml).

The resulting solution of $H_2O_2$ and propionic aldehyde cooled to 0° C. (75 ml of distilled water are cooled to 0° C. and 3.3 ml of 32% $H_2O_2$ and 5 ml of propionic aldehyde are added) and incubated in a smooth flowing manner for 150 min. The reaction product (i.e. irinotecan) is diluted with water to a volume of 3 l and transferred to chromatographic purification (Diaion sorbent resin).

Example 3

20 g of Irinotecan are diluted in aqueous solution of sulfuric acid (400 ml of 40% $H_2SO_4$). $FeSO_4 \times 7H_2O$ (10.5 g) is added at 20° C., and the solution is cooled to −10° C. C before propionic aldehyde is added (10 ml). The resulting solution of $H_2O_2$ and propionic aldehyde cooled to 0° C. (75 ml of distilled water are cooled to 0° C. and 3.3 ml of 32% $H_2O_2$ and 5 ml of propionic aldehyde are added) and incubated in a smooth flowing manner for 150 min. 11-ethyl-irinotecan is not detected during analysis of the reaction product by means of HPLC.

Example 4

When comparing the method of the present invention as illustrated in FIG. 3 with two methods for the synthesis of irinotecan that are established in the art (illustrated in FIG. 1 and FIG. 2, respectively) with respect to the numbers and types of unwanted reaction products it becomes immediately evident that the method of the present invention provides for superior results. The findings are summarized in the following table.

Figure 2:
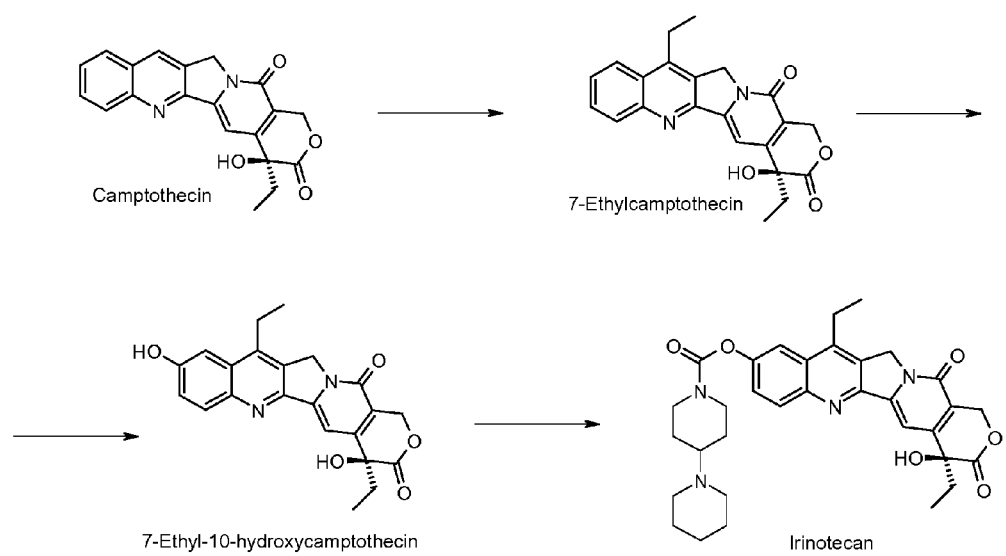
FIG. 2: Schematic representation of an alternative established synthesis route for the preparation of 7-ethyl-10-[4-(1-piperidino)-1-piperidino]carbonyloxy-camptothecin that uses camptothecin as starting material and 7-ethylcamptothecin as intermediate.

| Compound name | Function in the process according to | | |
| --- | --- | --- | --- |
| | FIG. 1 | FIG. 2 | FIG. 3 |
| 10-hydroxycamptothecin | intermediate | virtually absent | starting material |
| irinotecan enantiomer | by-product | by-product | by-product |
| 7-des-ethyl irinotecan | by-product | by-product | intermediate |
| 7-ethyl-10-hydroxycamptothecin | virtually absent | intermediate | virtually absent |
| 11-ethyl irinotecan | by-product | by-product | virtually absent |
| 7-ethyl-camptothecin | virtually absent | intermediate | virtually absent |
| 7,11-diethyl-10-hydroxycamptothecin | by-product | by-product | virtually absent |
| camptothecin | starting material | starting material | virtually absent |

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method for the synthesis of 7-ethyl-10-[4-(1-piperidino)-1-piperidino]carbonyloxycamptothecin having the structure according to Formula (1), the method comprising:

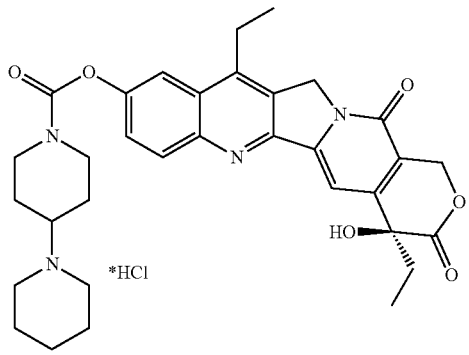

Formula 1

Irinotecan (a) preparing 10-[4-(1-piperidino)-1-piperidino]carbonyloxycamptothecin by contacting 10-hydroxycamptothecin with chlorocarbonyl-4-piperidinopiperidine hydrochloride; and
(b) selectively ethylating the compound obtained in step (a) at the 7-position, thus resulting in the preparation of 7-ethyl-10-[4-(1-piperidino)-1-piperidino]carbonyloxycamptothecin.

2. The method of claim 1, wherein step (a) is performed in acetonitrile in the presence of at least one alkali metal carbonate or of a strong organic base.

3. The method of claim 2, wherein step (a) is performed in the presence of an alkali metal carbonate selected from the group consisting of $Na_2CO_3$, $K_2CO_3$, $Rb_2CO_3$, and $Cs_2CO_3$.

4. The method of claim 2, wherein step (a) is performed in the presence of a strong organic base and wherein said strong organic base is triethylamine.

5. The method of claim 1, wherein step (a) is performed at a temperature in the range between 20° C. and 80° C.

6. The method of claim 1, wherein step (b) is performed in the presence of ferrous sulfate, hydrogen peroxide, and propionic aldehyde.

7. The method of claim 5, wherein step (a) is performed at a temperature of 60° C.

* * * * *